United States Patent
Hedges

(10) Patent No.: US 9,702,862 B2
(45) Date of Patent: Jul. 11, 2017

(54) DETECTION OF FUEL CONTAMINATION IN LUBRICATING OIL

(71) Applicant: Voelker Sensors, Inc., Palo Alto, CA (US)

(72) Inventor: Joe D. Hedges, Portola Valley, CA (US)

(73) Assignee: Voelker Sensors, Inc., Palo Alto, CA (US)

(*) Notice: Subject to any disclaimer, the term of this patent is extended or adjusted under 35 U.S.C. 154(b) by 395 days.

(21) Appl. No.: 14/159,807

(22) Filed: Jan. 21, 2014

(65) Prior Publication Data

US 2014/0130579 A1    May 15, 2014

Related U.S. Application Data

(63) Continuation of application No. 12/857,747, filed on Aug. 17, 2010, now Pat. No. 8,643,388, which is a continuation-in-part of application No. 12/426,956, filed on Apr. 20, 2009, now Pat. No. 7,928,741, which is a continuation of application No. 11/676,738, filed on Feb. 20, 2007, now Pat. No. 7,521,945.

(60) Provisional application No. 60/782,959, filed on Mar. 15, 2006, provisional application No. 60/774,749, filed on Feb. 17, 2006.

(51) Int. Cl.
   *G01N 33/28* (2006.01)

(52) U.S. Cl.
   CPC .................... *G01N 33/2888* (2013.01)

(58) Field of Classification Search
   CPC .................................................. G91N 33/2888

USPC .................... 324/698; 73/53.05, 54.24, 61.43
See application file for complete search history.

(56) References Cited

U.S. PATENT DOCUMENTS

| | | |
|---|---|---|
| 2,862,859 A | 12/1958 | Grosskopf |
| 3,182,255 A | 5/1965 | Hopkins et al. |
| 3,386,859 A | 6/1968 | Biddick |
| 3,410,780 A | 11/1968 | Holden |
| 3,787,650 A | 1/1974 | Lewis |
| 4,007,629 A | 2/1977 | Hochstein |
| 4,345,202 A | 8/1982 | Nagy et al. |
| 4,443,754 A | 4/1984 | King |
| 4,606,222 A | 8/1986 | Stockmeyer |
| 4,646,070 A | 2/1987 | Yasuhara et al. |
| 4,679,007 A | 7/1987 | Reese et al. |

(Continued)

FOREIGN PATENT DOCUMENTS

| | | |
|---|---|---|
| EP | 0442314 | 8/1991 |
| EP | 0584557 | 7/1992 |

(Continued)

OTHER PUBLICATIONS

Allen, Mike, "Dirty Deeds Done Dirt Cheap," Car Clinic, Car Care, Popular Mechanics, Aug. 1993, p. 71.

(Continued)

*Primary Examiner* — Vincent Q Nguyen
(74) *Attorney, Agent, or Firm* — Polsinelli LLP

(57) ABSTRACT

A method for measuring fuel contamination in oil that uses a material in contact with oil whereby fuel intrusion into the oil will change the electrical, mechanical, and/or chemical properties of the material as compared to the same electrical, mechanical, and/or chemical properties of the material when in contact only with mineral or synthetic oil only.

18 Claims, 8 Drawing Sheets

(56) References Cited

U.S. PATENT DOCUMENTS

| | | | |
|---|---|---|---|
| 4,733,556 A | 3/1988 | Meitzler et al. | |
| 4,764,258 A | 8/1988 | Kauffman | |
| 4,791,374 A | 12/1988 | Yodice et al. | |
| 4,857,829 A | 8/1989 | Sagae et al. | |
| 4,872,316 A | 10/1989 | Browne et al. | |
| 4,952,868 A | 8/1990 | Scherer, III | |
| 5,071,527 A | 12/1991 | Kauffman | |
| 5,089,780 A | 2/1992 | Megerle | |
| 5,141,717 A | 8/1992 | McRae | |
| 5,435,170 A | 7/1995 | Voelker et al. | |
| 5,739,916 A * | 4/1998 | Englehaupt | G01N 21/31 356/414 |
| 5,777,210 A | 7/1998 | Voelker et al. | |
| 5,789,665 A | 8/1998 | Voelker et al. | |
| 5,824,889 A * | 10/1998 | Park | G01N 33/2888 324/378 |
| 6,261,455 B1 * | 7/2001 | Brown | B04B 1/06 210/167.02 |
| 6,286,363 B1 | 9/2001 | Discenzo | |
| 6,463,967 B1 | 10/2002 | Boyle | |
| 6,873,916 B2 | 3/2005 | Kolosov et al. | |
| 7,521,945 B2 | 4/2009 | Hedges et al. | |
| 7,928,741 B2 | 4/2011 | Hedges | |
| 8,614,588 B2 | 12/2013 | Hedges | |
| 8,643,388 B2 | 2/2014 | Hedges | |
| 2001/0053750 A1 | 12/2001 | Ogano et al. | |
| 2003/0147073 A1 | 8/2003 | Abraham et al. | |
| 2003/0222656 A1 | 12/2003 | Phillips et al. | |
| 2004/0036487 A1 | 2/2004 | Heremans et al. | |
| 2004/0050188 A1 | 3/2004 | Richards et al. | |
| 2004/0178900 A1 | 9/2004 | Berndorfer et al. | |
| 2004/0212378 A1 | 10/2004 | Sohl et al. | |
| 2004/0257094 A1 | 12/2004 | Halalay et al. | |
| 2004/0263187 A1 | 12/2004 | Hayashi et al. | |
| 2005/0145033 A1 | 7/2005 | Bossi et al. | |
| 2006/0003882 A1 | 1/2006 | Smith | |
| 2006/0229776 A1* | 10/2006 | Lvovich | G01N 33/2888 324/698 |
| 2007/0029121 A1 | 2/2007 | Saitou et al. | |
| 2007/0194801 A1 | 8/2007 | Hedges et al. | |
| 2008/0228339 A1 | 9/2008 | Rains et al. | |
| 2009/0216464 A1 | 8/2009 | Kong | |
| 2009/0234533 A1 | 9/2009 | Trinkner | |
| 2011/0169512 A1 | 7/2011 | Hedges | |
| 2011/0267080 A1 | 11/2011 | Hedges | |
| 2012/0180555 A1 | 7/2012 | Hedges | |
| 2014/0130900 A1 | 5/2014 | Hedges | |

FOREIGN PATENT DOCUMENTS

| | | | |
|---|---|---|---|
| GB | 939049 | | 10/1963 |
| JP | 2007066968 A | * | 3/2007 |
| WO | WO 9219848 | | 11/1992 |
| WO | WO 95/18370 | | 7/1995 |
| WO | WO 2007/098213 | | 8/2007 |

OTHER PUBLICATIONS

"Assured Oil Performance at a Glance," Voelker Sensors Inc., 2004.
Bowman, W.R., "Application of Sealed Capsule Differential Scanning Calorimetry-Par II: Assessing the Performance of Antioxidants and Base Oils ©" Technical Paper, Lubrication Engineering, May 1999, pp. 22-29.
Bowman, W.F., "Application of Sealed Capsule Differential Scanning Calorimetry-Part I: Predicting the Remaining Useful Life of Industry-Used Turbine Oils ©," Journal of the Society of Tribologists and Lubrication Engineers, Aug. 18, 1998, pp. 19-24.
Changes in Physical and Chemical Properties of Shortenings Used for Commercial Deep-Fat Frying. Aug. 1986.
Dong, Jung., "Rapid Determination of the Carboxylic Acid Contribution to the Total Acid Number of Lubricants by Fourier Transform Infrared Spectroscopy ©," Technical Paper, Journal of the Society of Tribologists and Lubrication Engineers, Aug. 30, 1999, pp. 12-20.
"Engine Fuel Oil Monitoring System:" Flotech Process Control & Implementation. Copyright © 2010. <http://www.flotech.com.sg/systems/marine-offshore/engine-fuel-oil.html>.
Kauffman, R.E., "Rapid, Portable Voltammetry Techniques for Performing Antioxidant, Total Acid Number (TAN) and Total Base Number (TBN) Measurements ©," Technical Papers, Journal of the Society of Tribologists and Lubrication Engineers, Jan. 1998, pp. 39-46.
Lee, Han-Sheng, "In-Situ Oil Condition Monitoring in Passenger Cars ©," Journal in Society of Tribologists and Lubrication Engineers, 1993, vol. 50, No. 8, pp. 605-611.
Mookken, R.T., "Dependence of Oxidation Stability of Steam Turbine Oil on Base Oil Composition ©," Journal of the Society of Tribologists and Lubrication Engineers, Dec. 3, 1996, pp. 19-24.
"Oil Advantage: In-line Oil Monitoring System," Voelker Sensors Inc., 2004.
"Oil Advantage: Low Cost In-line Oil Monitoring System," Voelker Sensors Inc., 2006, VSI.
"Product—The Rocket Wireless Gauge: The OEM Rocket Wireless Full Level Monitor." OEM Oil Equipment Manufacturing LLC. Accessed: Apr. 13, 2011. <http:www.oil-equip-mfg.com/docs/productsrocket.html>.
Sato, Atsushi, "Electrical Conductivity Method for Evaluation of Oxidative Degradation of Oil Lubricants ©," Journal of the Society of Tribologists and Lubrication Engineers, Jul. 1992, vol. 48, No. 7, pp. 539-544.
Sullivan, Tim, "Oil Sludge Bedevils VW," Lube Report, Aug. 31, 2004, http://www.lubereport.com/e_article000298526.cfm?x=b3t4ghV,bhb871W.
White, Elecia, "Due for an Oil Change?" Putting Sensors to Work, Sensors, Apr. 2005, pp. 27-29.
"Wireless technology reduces installation cost for floating roof temperature measurement applications and establishes communications network for future expansion." Emerson Process Management. Jan. 6, 2010. <http://www.2emersonprocess.com/en-US/news/pr/Pages/1001-BPDalmery.aspx>.
PCT Application No. PCT/US94/13779, International Search Report mailed Mar. 24, 1995.
PCT Application No. PCT/US07/04529, International Search Report and Written Opinion mailed Mar. 11, 2008.
U.S. Appl. No. 11/676,738; Office Action mailed Nov. 3, 2008.
U.S. Appl. No. 12/426,956, Final Office Action mailed Aug. 5, 2010.
U.S. Appl. No. 12/426,956, Office Action mailed Mar. 4, 2010.
U.S. Appl. No. 12/857,747; Final Office Action mailed Jul. 10, 2013.
U.S. Appl. No. 12/857,747; Office Action mailed Mar. 21, 2013.
U.S. Appl. No. 12/857,747; Final Office Action mailed Nov. 19, 2012.
U.S. Appl. No. 12/857,747; Office Action mailed Sep. 11, 2012.
U.S. Appl. No. 12/953,377; Final Office Action mailed Oct. 31, 2013.
U.S. Appl. No. 12/953,377; Office Action mailed Mar. 18, 2013.
U.S. Appl. No. 13/212,174; Office Action mailed Mar. 27, 2013.
U.S. Appl. No. 12/953,377; Office Action mailed May 14, 2014.
U.S. Appl. No. 14/140,342; Office Action mailed Jun. 2, 2016.
U.S. Appl. No. 14/140,342, filed Dec. 24, 2013, Joe Hedges, Active Filtering of Oil.

* cited by examiner

Relative Low Conductivity

Relative High Conductivity

DETECTION OF FUEL CONTAMINATION IN LUBRICATING OIL

CROSS-REFERENCE TO RELATED APPLICATIONS

The present application is a continuation and claims the priority benefit of U.S. patent application Ser. No. 12/857,747 filed Aug. 17, 2010, now U.S. Pat. No. 8,643,388 that issued on Feb. 4, 2014, which is a continuation-in-part and claims the priority benefit of U.S. patent application Ser. No. 12/426,956 filed Apr. 20, 2009, now U.S. Pat. No. 7,928,741, which is a continuation and claims the priority benefit of U.S. patent application Ser. No. 11/676,738 filed Feb. 20, 2007, now U.S. Pat. No. 7,521,945, which claims the priority benefit of U.S. provisional application 60/782,959 filed Mar. 15, 2006 and U.S. provisional application 60/774,749 filed Feb. 17, 2006, the disclosures of which are incorporated herein by reference.

U.S. patent application Ser. No. 12/857,747 is related to U.S. patent application Ser. No. 08/176,393 filed Dec. 30, 1993, now U.S. Pat. No. 5,435,170, U.S. patent application Ser. No. 08/730,109 filed Oct. 15, 1996, now U.S. Pat. No. 5,777,210, and U.S. patent application Ser. No. 08/637,878 filed Apr. 25, 1996, now U.S. Pat. No. 5,789,665, the disclosures of which are incorporated herein by reference.

BACKGROUND OF THE INVENTION

Field of the Invention

The present invention generally relates to detecting fuel contamination in lubricating oil. More specifically, the present invention relates to in-situ fuel contamination detection to prevent catastrophic failure of engine or other moving parts.

Description of the Related Art

Fuel contamination in crankcase oil decreases the lubricating ability of oil and will lead to engine failure. If a fuel injector becomes stuck in the open position, the introduction of large amounts of fuel in crankcase oil will decrease the viscosity of the oil. If the fuel contamination goes undetected, the decrease in viscosity will cause a loss of hydrodynamic lubrication resulting in metal to metal contact and ultimately causing spun and/or seized bearings.

Current methods for fuel detection include absorption spectroscopy, viscosity, and the use of a 'sniffer' to measure the aromatics in the gas above the oil. Fuel contamination can be detected using absorbance spectroscopy, but the method has been developed for bench top measurements after a sample of oil has been removed from the crankcase. The difficulties in applying absorbance spectroscopy to an in-situ device are significant and make this particular detection technique impractical. Alternatively, and in the absence of other contaminants in the oil or chemical changes to the oil, fuel (in large enough quantities) can be detected by measuring the viscosity of the oil by comparing to the original oil viscosity. However, oil wear, water contamination, and soot contamination all cause an increase the viscosity of the oil making the detection of fuel contamination in oil by measuring its viscosity difficult. A sniffer requires constant calibration with a known fuel/oil mixture which is impractical in an in-situ device. Still further, fuel does not significantly change other measurable qualities of the oil (conductivity, dielectric constant, resistance, capacitance, polarity, TAN, TBN, etc.) so a direct in-situ electrical or chemical measurement of the oil to detect the presence of fuel is difficult.

An in-situ fuel contamination detection sensor is needed for early detection of fuel contamination in order to prevent catastrophic failure.

SUMMARY OF THE PRESENTLY CLAIMED INVENTION

In one embodiment of the present invention, a method for measuring fuel contamination in oil is disclosed. Through the method, an electrical, mechanical, and/or chemical property of a material in contact with oil is measured. The measured electrical, mechanical, and/or chemical property of the material in contact with the oil is compared against a previously measured electrical, mechanical, and/or chemical property of the same material. A change is identified in the measured electrical, mechanical, and/or chemical property against the previously measured electrical, mechanical, and/or chemical property, wherein the change indicates fuel intrusion into and contamination of the oil.

DETAILED DESCRIPTION

Figure 1:
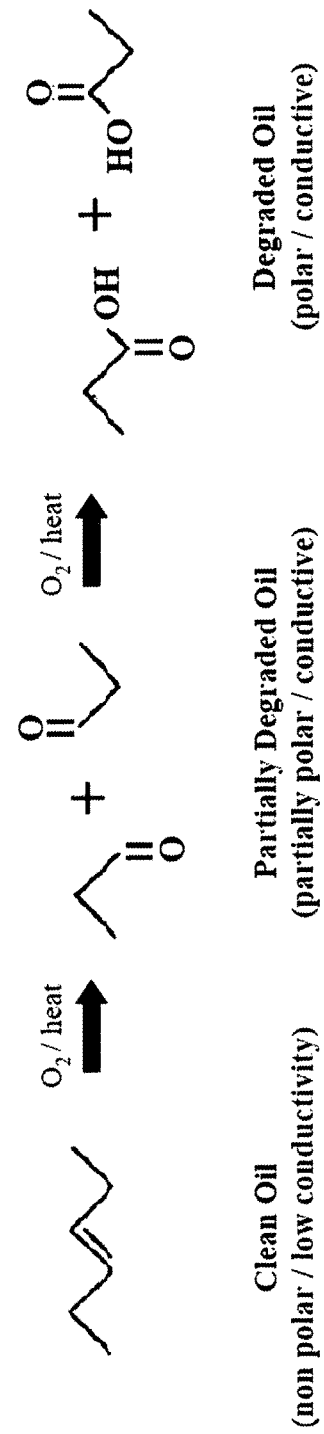
FIG. 1 illustrates the wear of oil due to oxidation and heat whereby the oil becomes more polar as is known in the prior art.

Embodiments FIG. 1 illustrates oil that, initially, is clean and non-polar. In the presence of $O_2$ and heat, the oil begins to degrade. This application of $O_2$ and heat would occur through, for example, the normal and ongoing use of the oil in an automobile. This partially degraded oil, as also shown in FIG. 1, begins to take on polar characteristics. Through the continued application of $O_2$ and heat, the oil becomes even more degraded and takes on even greater polar characteristics as further shown in FIG. 1. Increased polarity causes the oil to change is dielectric constant, which in turn leads to increased capacitance.

Figure 2:
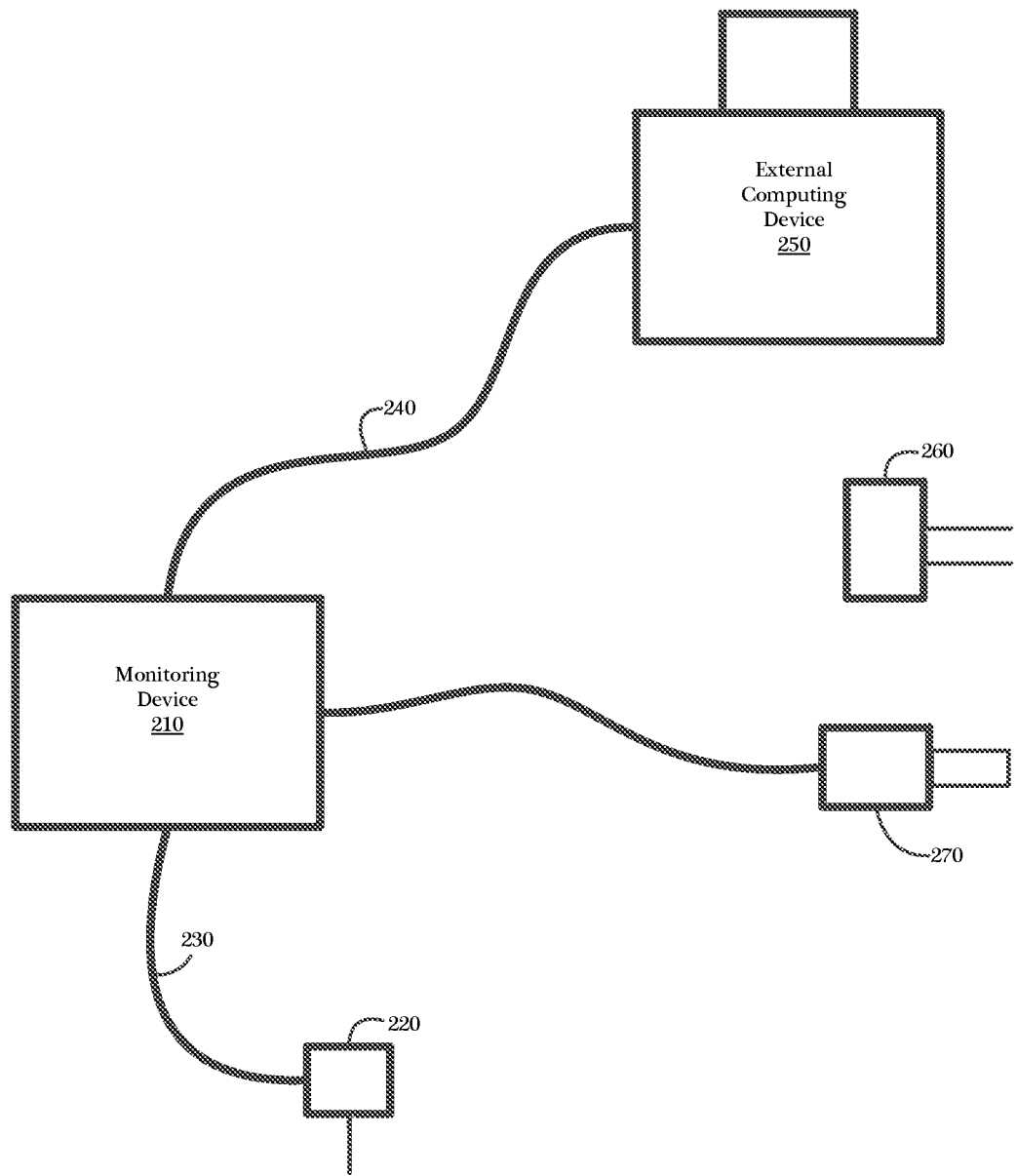
FIG. 2 illustrates an exemplary real-time oil monitoring system as may be implemented in accordance with an embodiment of the present invention.

FIG. 2 illustrates an exemplary real-time oil monitoring system 200 as may be implemented in accordance with an embodiment of the present invention. An embodiment of the oil monitoring system 200 may comprise a monitoring device 210 for receiving and analyzing data generated by a sensing element 220, which is in contact with the oil or other fluid under observation.

Data generated by the sensing element 220 may be communicated to the monitoring device 210 via a sensor signal cable 230. Sensor signal cable 230, in one embodiment of the present invention, is an RS-232 compliant serial cable wherein one end of the cable is configured to exchange data with the monitoring device 210 and the opposite end of the cable is configured to interface with sensing element 220 as is discussed in greater detail in FIG. 3. Other data cables are within the scope of the present invention subject to proper configuration to allow for interface with the sensing element 220 and monitoring device 210.

Monitoring device 210 may be further communicatively coupled to an external computing device 250 such as a laptop computer, a PDA or other mobile computing device that may be specially configured for use with the oil sensing element 220 and monitoring device 210. While mobility of the external computing device 250 may be preferred in some environment (e.g., a garage), it is within the scope of the present invention for the external computing device 250 to be a less-portable computing device such as a dedicated workstation or desktop computer. Data may be exchanged between the monitoring device 210 and external computing device 250 through, for example, an external data cable 240 or a wireless network connection.

External data cable 240 may comply with any number of data transmission standards including Universal Serial Bus (USB) and IEEE 1394 in addition to being a parallel or serial data cable. In some embodiments of the present invention, monitoring device 210 may be configured for the introduction of, for example, a PCMCIA wireless card or other wireless network adapter. In such an embodiment, the monitoring device 210 may communicate data gathered from the sensing element 220 as well as data analyzed by the monitoring device 210 wirelessly using, for example, the 802.11x wireless data standard to external computing device 250 such that external data cable 240 is no longer necessary.

A wireless configuration of this nature would allow increased mobility of the monitoring device 210 while still allowing, for example, for the storage of oil data in a centralized repository such as the aforementioned external computing device 250. Storage of oil measurement data and analyses of that data may be useful in determining if a particular vehicle or combustion engine might be suffering from engine damage or some other defect in that the particular vehicle or engine prematurely degrades oil. Such information may be reflected by a series of oil analyses conducted over time. These analyses may be stored, further analyzed, and graphically illustrated in a report or some other organized information presentation generated by external computing device 250. It should be noted that the presence of an external computing device 250 is not required for the operation of the monitoring device 210 in conjunction with sensing element 220.

The monitoring device 210, in one embodiment of the present invention, receives and displays data indicative of the status of the oil or another fluid under observation and analysis. The interface of monitoring device 210 is discussed in more detail in FIG. 7 below.

Monitoring device 210 and certain devices coupled to device 210 may be powered by a variety of electrical power sources. In one embodiment of the present invention, monitoring device 210 may be electrically coupled to an AC transformer 260. In another embodiment of the present invention, monitoring device 210 may be electrically coupled to a DC transformer such as a cigarette lighter adaptor whereby the system 200 may be used 'on-the-road' through use of an automobile's cigarette lighter power outlet. Monitoring device 210 may further be powered by a replaceable or rechargeable battery pack (not shown).

In an embodiment of the present invention, the monitoring device 210 may also comprise a thermistor configured to be used by a microprocessor in the device 210 to compensate sensor readings for thermal variations. For example, in one embodiment of the present invention, the system 200 may only operate at engine operating temperatures in excess of, for example, 70° C. as the conductivity of certain oils may be completely masked by the additives below that temperature. Additionally, because oil is formulated to work at automotive operating temperatures, the oil may not properly lubricate at lower temperatures thereby distorting data gathered by the sensing element 220.

Figure 3:
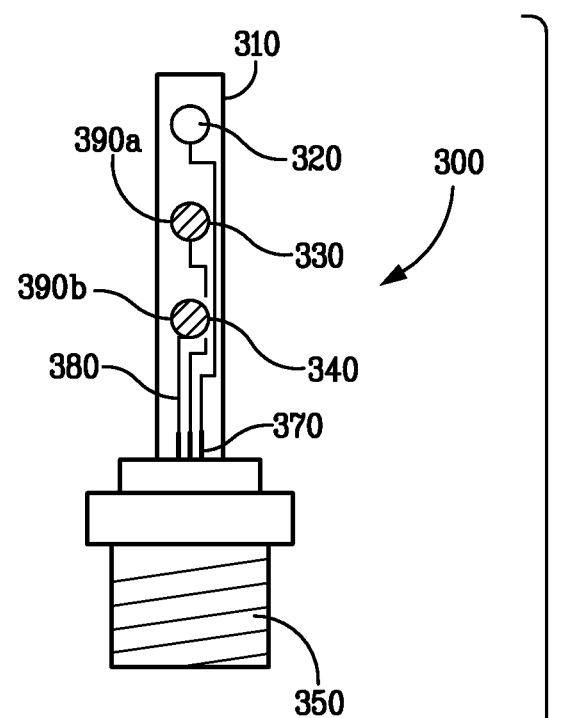
FIG. 3 illustrates an exemplary embodiment of a sensing element as may be used in the present invention in addition to an inset reflecting the installation of the sensing element in an oil pan.
Figure 3:
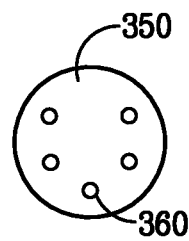
Figure 3:
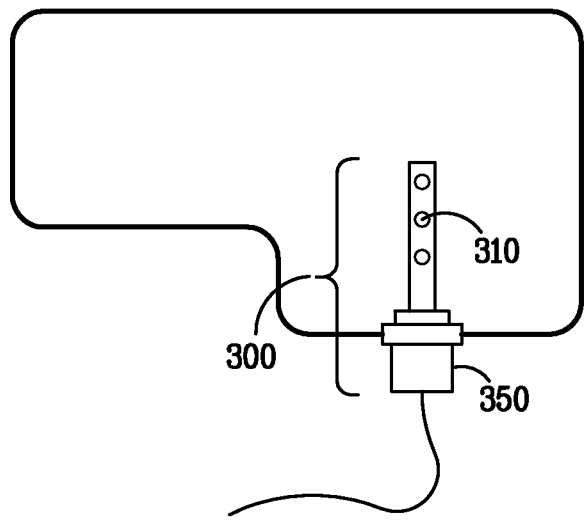

FIG. 3 illustrates an exemplary embodiment of a sensing element 300 as may be used in the present invention. The inset of FIG. 3 reflects the sensing element 300 having been installed in an oil pan. Sensing element 300 comprises an electrically nonconductive housing 310 with three chambers (320, 330, and 340). Examples of non-conductive materials for constructing the housing 310 include but are not limited to ceramic, glass, plastic, woven fiberglass, and paper impregnated with phenolic resin (e.g., Pertinax).

In some embodiments of the present invention, the housing 310 may be constructed of an electrically non-conductive material. In other embodiments, the housing 310 may instead be constructed of one or more materials (which may or may not be electrically non-conductive) and subsequently coated with an electrically non-conductive material such as a non-conductive resin cured with ultraviolet light and/or heat. In addition to non-conductive resins, other suitable coating materials include but are not limited to tape, paints and hot melt adhesives.

Housing 310 may be mounted in a conventional drain plug 350 such that the sensing element 300 may be installed in a conventional oil pan of an internal combustion engine. Mounting of the housing 310 may occur utilizing various industrial glues, sealants, adhesives or other means so long as such mounting means do not interfere with the sensing element 300's ability to communicate with cable connector pins 360 as discussed in greater detail below.

By mounting the housing 310 of the sensing element 300 in a conventional drain plug 350, an embodiment of the present invention may be installed in older automobiles or equipment utilizing a combustion engines without the need for extensive retrofitting as the drain plug 350 may simply be threaded into the oil pan's drain hole as would occur when changing the oil of a car. An embodiment of drain plug 350 used for mounting the housing 310 of the sensing element 300 may utilize ½"×20 threading such than an exemplary sensing element 300 measuring approximately 2.8" in length occupies an internal depth of approximately 1.8".

The particular mechanical interface (e.g., shape and threading specifications) of the aforementioned drain plug 350 are exemplary as are the particular dimensions of the sensing element 300. The drain plug 350 may utilize any variety of physical configurations (e.g., hex nut) and threading arrangements and may further be specially manufactured for particular combustion engine/oil pan/engine environments. The sensing element 300 (as a part of or independently of the drain plug 350) may also utilize any variety of O-rings, washers, and/or protective housings in order to properly protect the sensing element 300 and to otherwise ensure that housing 310 is properly secured within the drain plug 350.

Figure 4:
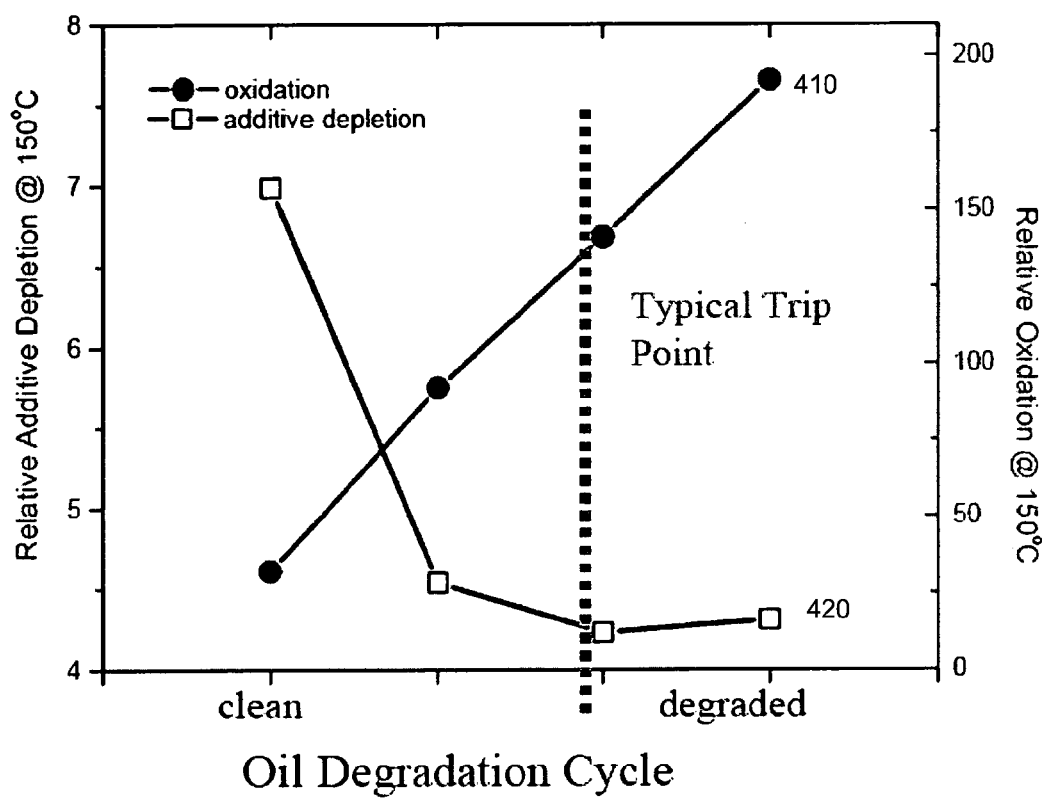
FIG. 4 is an exemplary illustration of the oil degradation cycle.

One of the three chambers of sensing element 300 (e.g., chamber 320) is open. Chamber 320 detects the conductivity of the oil directly. With regard to chamber 320, conductivity is dominated by the ionic characteristics of oil additives (oxidation 410) as is shown in the exemplary oil degradation cycle depicted in FIG. 4. In the oil degradation cycle of FIG. 4, as additives are depleted the additives become less polar; as the base oil itself deteriorates, the base oil becomes more polar.

Returning to FIG. 3, the remaining two chambers (chambers 330 and 340) are covered by a conductive mesh screen (390*a* and 390*b*). Chamber 330 comprises (houses) a matrix of insoluble polymeric beads (not shown). Chamber 340 comprises a single bead (not shown). The conductive mesh screen (390*a* and 390*b*) may be constructed of stainless steel cloth.

Figure 5A:
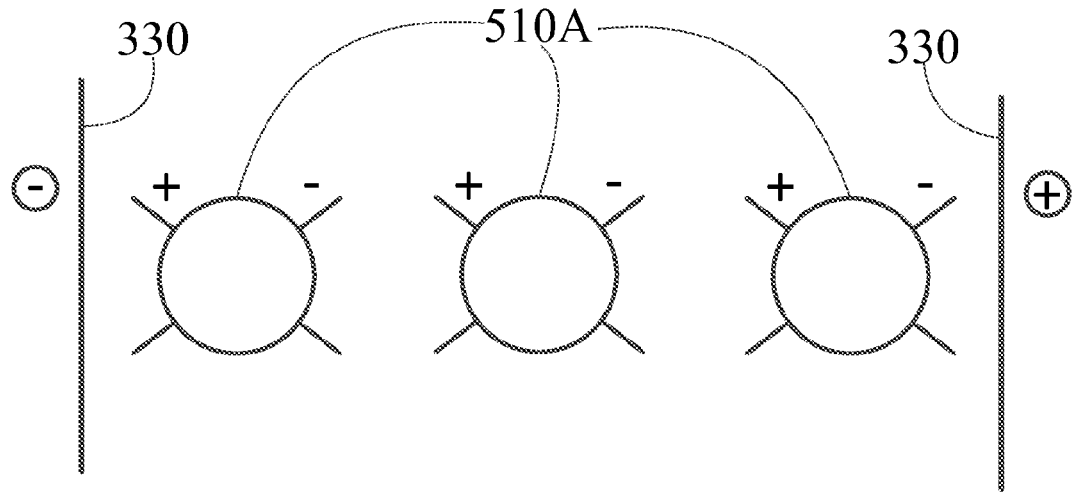
FIG. 5A is an exemplary illustration of polymeric bead interaction in a non-polar oil solution representative of relatively low conductivity in an exemplary embodiment of the present invention.
Figure 5B:
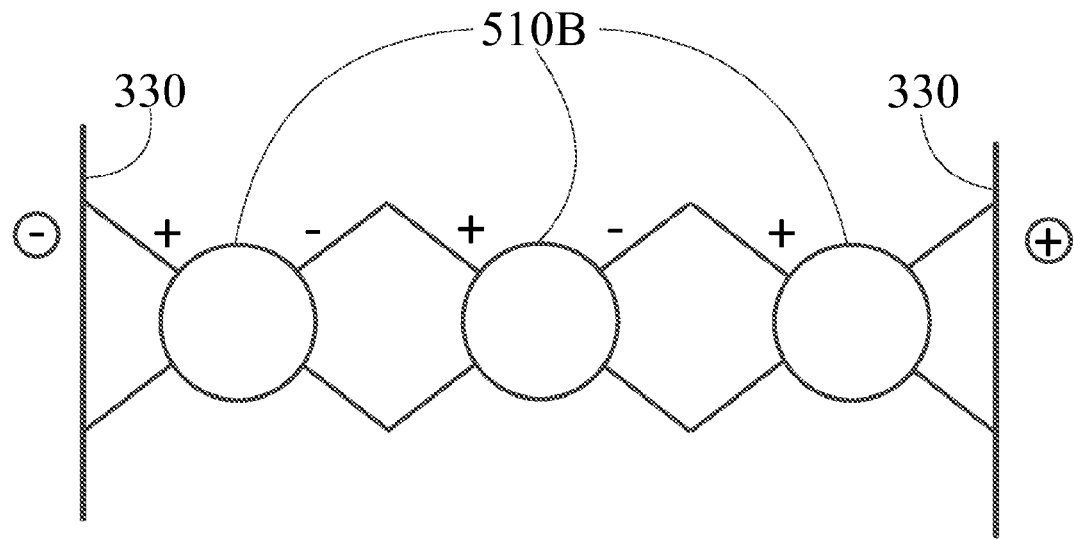
FIG. 5B is an exemplary illustration of polymeric bead interaction in a polar oil solution representative of relatively high conductivity in an exemplary embodiment of the present invention.

In a non-polar solution with relatively low conductivity, the beads 510A in chamber 330 remain separate from one another as is shown in FIG. 5A. It should be noted that in FIG. 5A as well as FIG. 5B—for the sake of simplified illustration—only a single monolayer of the charged bead matrix is shown. The fact that only a single monolayer is illustrated should not be interpreted as otherwise limiting the present disclosure. As the oil's polarity increases, however, the conductivity across the matrix increases and the ionic component of each group of beads relaxes 510B and begins electrically interacting with an adjacent group in the presence of voltage potential. FIG. 5B illustrates the same whereby the beads form a bridge on the conductive mesh 390*a* of the chamber 330. The change in the bead matrix as illustrated in FIGS. 5A and 5B indicates both additive depletion and oxidation and is represented graphically by line 420 (additive depletion) in FIG. 4.

The sensing element 300 generates a sensor reading reflective of oxidation based on a differential measurement of a matrix of insoluble polymeric beads and the oil being analyzed. Sensing element 300 further generates a sensor reading reflective of the presence of soot and similar contaminants based on a differential measurement of oil inside a filter and the oil being analyzed. Sensing element 300 further generates a sensor reading reflective of the presence of fuel, water or similar contaminants based on a differential measurement of a matrix of insoluble polymeric beads and the contaminated oil being analyzed. The sensing element 300 may measure oil quality through the use of any one of a number of different electrical forms including alternating current (AC), direct current (DC), a combination of AC/DC, in addition to mechanical forms such as crystal resonance. By utilizing sensor readings from the three chambers of the sensor array, an accurate measurement of oxidation, additive depletion, and contamination is provided, which is more accurate reflection of oil quality.

Data readings from open chamber 320 are subtracted from data readings obtained from the bead matrix in chamber 330. This subtraction of data may take place in a differential analysis software module (not shown) in monitoring unit 210 under the control of a microprocessor (also not shown). Various other hardware and software elements may be present in monitoring unit 210 to allow for the receipt, processing, analysis, storage, and/or exchange of data. For example, one embodiment of the present invention may utilize an application specific integrated circuit (ASIC) for undertaking the differential analysis otherwise performed by the aforementioned software module. Through the subtraction of the open chamber 320 data, effects of additives are removed from the analysis and only oxidation is measured. In this regard, no calibration of the system 200 is required and any differences in various oil formulations are negligible with regard to a determination of oxidation in the oil under analysis.

This differential measurement technique may be used to determine the polarity of oil where one chamber measures multiple properties of the oil and a second chamber measures the same properties with the exception that it does not measure the polarity of the oil. Taking a differential measurement between the two chambers allows for a determination of the polar condition of the oil. Specifically, if an electrical measurement of the oil is made and a second electrical measurement is made of an ionic polystyrene matrix where the electrical signal includes components from both the oil and the polystyrene matrix then the difference between the signals shows the polarity of the oil.

Chamber 330 may determine soot contamination in an oil sample wherein the sensing element 300 has been disposed. Soot particulates consist primarily of carbon and tend to bind to one another and to the actual engine. If soot is allowed to aggregate unfettered, the soot particulates can actually begin to score the engine bearings. Soot measurement is based on a percentage of the amount of soot freely available in the oil and is commonly referred to as the saturated relative contamination. A given amount of free soot can, in some instances, constitute 1% to 2% contamination for base oil without additives or greater than 7% for fully formulated oils.

When a soot dispersant additive begins to fail, the soot begins to adhere to the surface of the aforementioned polymeric beads and form a bridge across the chamber 330. When such a bridge occurs, sensor readings at chamber 330 change dramatically and continue to increase as more layers of carbon soot accumulate. Conductivity caused by soot is considerably greater than that due to oil and additive polarity and is measurable by the present sensing element 300 in addition to capable of being differentiated versus worn oil.

Soot contamination may be determined using a differential measurement. By using two chambers—one that measures the properties of the oil and the other that measures the properties of the oil after it has passed thru a fine filter that keeps soot or any other contaminates away from the sensor—soot contamination can be measured. Specifically, soot that is not chemically capped is electrically conductive. Taking the differential measurement of two chambers where one measures all the electrical characteristics of the oil and the other is precluded from measuring the effect of the soot (or any other particle) in the oil by a 0.2 micron filter allows for a determination of soot contamination. This technique is not limited to an electrical measurement; it could also be used in an optical measurement.

The third chamber—chamber 340—may detect water contamination in the oil or fluid under investigation. Water that enters the engine and boils as a result of engine temperature can cause the engine oil to turn into a sludge-like substance. This sludge-substance not only fails to properly lubricate various engine components but can also rust an engine from the inside-out.

A determination of water contamination in oil may be made using a differential measurement technique. By immersing two sensor chambers into the oil—one that measures multiple properties of the oil and the other measures multiple properties less the property associated with water contamination—and using a differential technique, the water contamination may be independently measured. Specifically, if an electrical measurement of polystyrene matrix is made where the matrix is relatively insensitive to water contamination and the signal is compared to a measurement of the polystyrene matrix that is highly sensitive to water absorption, the difference between the measurements will allow the water contamination to be measured.

The measurement may be made electrically or mechanically by looking at the change in electrical characteristics of the beads or by looking at the change in physical characteristics of the beads. Using a highly cross-linked polystyrene matrix will limit both the mechanical and electrical changes to the bead matrix. Using a loosely cross-linked polystyrene bead matrix will allow for large changes in the electrical and mechanical properties of the beads. The change is proportional to the quantity of water contamination.

Conventional methodologies report water in oil as a percentage of total volume. Different blends of oil, however, can consume varying amounts of water as a result of oil additives binding with water molecules. As such, an absolute measure of water it not necessarily helpful or informative. An embodiment of the present invention reports water content as a percent saturated relative humidity (SRH) of the oil. An SRH of, for example, 100% where the oil cannot absorb any more water without its dropping out of solution as emulsified or free water is the same for all oils at a given temperature.

As noted above, a single polystyrene bead 610A in chamber 340 measures water contamination corresponding to 2% SRH. The diameter of the bead is slightly less than the thickness of the sensor housing/sensor board 310. The bead 610B is extremely hydrophilic and attracts water, swells and physically contacts the conductive mesh screen 390b of the chamber 340. The resulting increase in conductivity is detected as shown in FIGS. 6A and 6B.

Figure 6A:
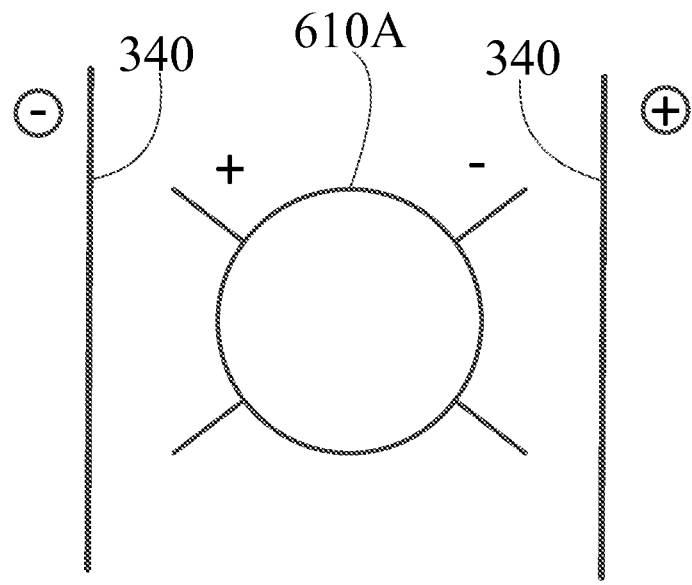
FIG. 6A illustrates a single hydrophilic, polystyrene bead in an environment without 'free' water and reflecting relatively low conductivity.
Figure 6B:
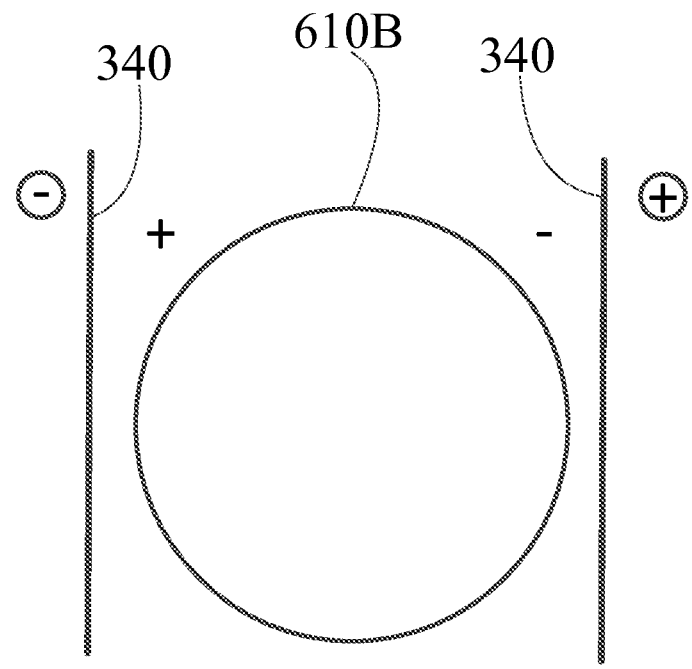
FIG. 6B illustrates a single hydrophilic, polystyrene bead in an environment with 'free' water and reflecting relatively high conductivity.

FIG. 6A illustrates a single hydrophilic, polystyrene bead 610A in an environment without 'free' water and reflecting relatively low conductivity. FIG. 6B, however, illustrates the same single hydrophilic, polystyrene bead in an environment with 'free' water (i.e., water contamination) whereby the bead 610B swells through its attracting of the 'free' water and comes into contact with camber 340's conductive mesh 390b) thus reflecting relatively high conductivity.

The polystyrene beads of the present invention may be impregnated with charged groups. In one exemplary embodiment, sodium and sulfite may be utilized as the cation and anion, respectively. Salts of polyatomic anions such as phosphates and carboxylates may also be utilized as cation exchange groups. Additionally, anionic exchange groups may comprise salts of N-alkylated amines. The beads may be cross linked with 8% divinylbenzene and further comprise a titer or exchange capacity of 1.7 meq/ml. The beads, further, may be of 1.180 to 38 µm in diameter; 500 mg of which being sufficient in the present invention although lesser (and greater) amounts are possible in the practice of the present invention (e.g., 20 mg).

The beads utilized in various embodiments of the present invention may be pre-treated or 'prepared' in order to create a polar environment that allows for more accurate measurement of conditions in a non-polar environment such as uncontaminated oil solutions.

Such a process may include washing the beads with 1N sodium hydroxide for approximately 15 to 30 minutes at room temperature; the excess sodium hydroxide is washed off in a methanol bath. The beads are further soaked in methanol to remove any excess water and then air dried to remove any remaining methanol. The beads are subsequently soaked in glycerol for approximately 24 hours and then heated to approximately 140° C. for approximately two hours to ensure proper penetration of the glycerol. At this point, the beads are fully swollen.

The beads are then placed in a non-polar fluid (e.g., clean oil) and again heated to 120° C. to remove excess ethylene glycol and to further 'shrink' the beads to a 'clean oil' state. The beads are then loaded into the various chambers (e.g., 330 and 340) of the sensing element 300. The beads are typically loaded into the various chambers (e.g., 330 and 340) of the sensing element 300 under slight to moderate pressure such that the beads are in close proximity to one another. In an alternative embodiment, the beads may be further soaked in glycerol to cause slight expansion of the beads and otherwise obtain bead-to-bead proximity.

Data readings from sensing element 300 are communicated to the monitoring device 210 of system 200 through any number of wire tracings 380 on/in the non-conductive housing 310 of element 300. The conductive pathways of the wire tracings 380 are, in some embodiments, etched from copper sheets laminated onto the non-conductive housing 310. In other embodiments, traces may be added through electroplating. Various other methodologies for creating the conductive wire tracings 380 on the non-conductive housing 310 including but not limited to silk screen printing, photoengraving, and milling. In some embodiments of the present invention, a series of layers of substrates may make up the non-conductive housing 310 and a series of blind and/or buried vias (not shown) may be used instead of (or in addition to) surface mount methodologies.

These conductive pathways are coupled (e.g., through soldering) to chambers 310-340 in addition to output connectors 370, which (in one embodiment of the present invention) extend outward from the drain plug 350 and toward the various elements on the face of the non-conductive housing 310 of sensing element 300. Output connectors 370 serve to couple the wire tracings 380 on the face of the non-conductive housing 310 to cable connector pins 360 which extend outward from the drain plug 350 (and away from the non-conductive housing 310) such that the connector pins 360 may be connected to sensor signal cable 230 for data exchanges with monitoring device 210. In this way, data generated at the various chambers 310-340 may be communicated through wire tracings 380 to the output connectors 370, which connect to cable connector pins 360.

In some embodiments, output connectors 370 and cable connector pins 360 may be the same uninterrupted element whereby the pins 360 extend through the drain plug housing 350 and toward the non-conductive housing 310 where one end of the connectors are soldered to the wire tracings 380. In additional embodiments of the present invention, that portion of the drain plug 350 most distant from the oil pan or chamber into which the non-conductive housing 310 is inserted may have a concave design such that the cable connector pins 360 are partially or entirely housed within the concave area and protected from damage through exposure to the elements that might corrode the face of the pins 360 or deform the shape of the pins 360 (e.g., bending) through impact or other applied forces.

Figure 7:
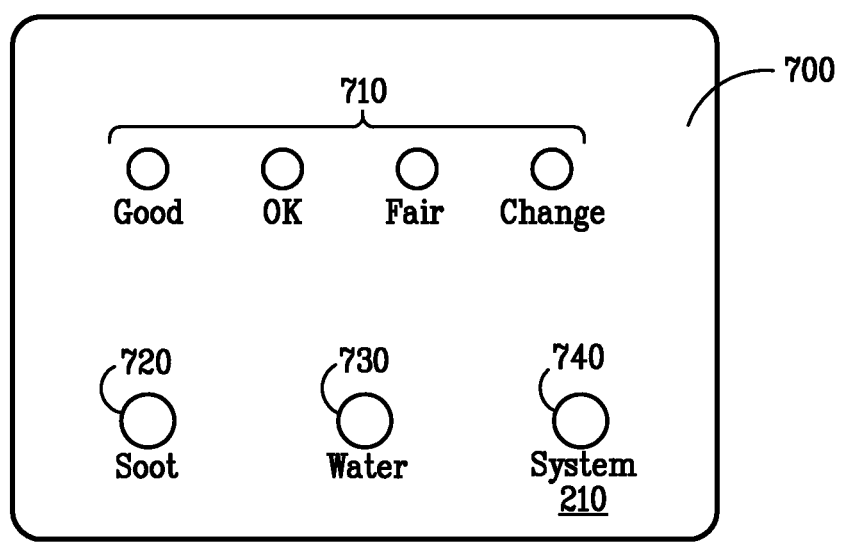
FIG. 7 illustrates an exemplary interface as may be used with a monitoring device of an exemplary embodiment of the presently disclosed oil monitoring system.

FIG. 7 illustrates an exemplary interface 700 as may be used with a monitoring device 210 of an exemplary embodiment of the presently disclosed oil monitoring system 200. After the aforementioned differential analysis software module of the monitoring device 210 has undertaken an analysis of the oil data from sensing element 220, the data is displayed in an informative format for the user of system 200.

For example, overall oil quality may be reflected by one of a series of light emitting diodes (LEDs) 710 in the monitoring device 210. Various levels of oil quality may be reflected although the present embodiment reflects levels of <good>, <ok>, <fair>, and <change>. The latter setting—<change>—indicates the poor quality of the oil under analysis and the need for a change of the same.

A similar LED may be utilized to reflect the presence of excess and unwanted soot in the oil under analysis (LED 720) as well as excess and unwanted water (LED 730). These indicators, too, may further or individually reflect the need to replace motor oil before damage to the engine environment ensues. An overall system status LED 740 indicates that the monitoring device 210 and related equipment is in overall working order and that 'false positives' reflecting inaccurate oil readings are not being generated.

In another embodiment of the present invention, the interface 700 of the monitoring device 210 may reflect a variety of graphical outputs. For example, oil quality may be reflected by an LED or digital image output bar that rises or falls based on the oil quality. Oil quality may also be reflected by a digital output reflecting a number indicative of oil quality such that increased quality accuracy is possible.

Data generated as a result of various oil measurements reflects the overall quality of the oil. For example, normal oil capacitance and normal oil conductivity in conjunction with no water absorption is generally an indicator of overall good oil quality. To the contrary, high oil capacitance, low oil conductivity in conjunction with no water absorption may indicate worn oil quality. Low capacitance and low conductivity of the oil may be reflective of additive depletion. Soot contamination and water contamination may be reflected by rapid increases in oil capacitance notwithstanding normal oil conductivity in conjunction with a lack of water absorption and the presence of water absorption, respectively.

Various differential measurement outputs (or specific measurements or ranges of measurement) may be correlated to the aforementioned interface outputs (i.e., good v. change; graphical bars; numerical output). In some embodiments, this information may also or, alternatively, be reflected at the external computing device 250.

In some embodiments of the present invention, a series or array of oil sensors 220 may be utilized. The collective measurement data is analyzed by a signal monitoring device 210 or may be collected by individual monitoring device 210 and subsequently conveyed to the external computing device 250. Through collection and analysis of oil quality data from a series or array of oil sensors 220, an even more accurate oil quality reading may be obtained in that irregular and/or inaccurate oil readings (e.g., spikes in data) may be identified and filtered out of the final oil quality analysis. The collective measurement data may be, for example, batched and collectively analyzed or serially analyzed as data becomes available. Parallel analysis of portions of the oil measurement data may also take place.

While the present invention has been described in connection with a series of exemplary embodiments, these descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art.

The aforementioned differential measurement techniques may also be used for measuring fuel contamination. Using two sensor chambers—one that is sensitive to fuel contamination and one that is not sensitive to fuel contamination—and taking the differential signal between the two allows the for the detection of fuel contamination in oil. This technique is not limited to the above examples but can also be used to measure specific additives, contaminates or differences in other types of base stocks. Further, the technique is not limited to measuring electrical properties. The technique may be used to measure a change in size of a polymeric matrix due to a change in polarity of the oil, change in chemical composition of the oil due to degradation or change in size of the matrix due to contamination.

Differential inputs may include beads prepared where one type of bead can have its ionic group influenced by metals whereas another group will not be influenced in such a manner. Alternatively, one group of beads may be prepared such that they react differently than another group of beads in the presence of fuel. Differential measurement combinations may take into account one or more of different bead types, bead cross-linking, bead size, and bead preparation; the ability to change the physical properties of the sensor chambers (e.g., filters, electrode size, electrode shape, and so forth); and electrical excitation possibilities.

Various embodiments of the present invention may be implemented to analyze a variety of oil types and viscosities. The present invention may be implemented to analyze fluid substances at a variety of temperatures. The present invention may further allow for retrofitting of older oil pans or combustion engines while further allowing for design-specific configurations. In some embodiments of the present invention, a sensing element may be dedicated to a particular oil quality determination and used in tandem with a series of other sensing elements with respect to differential measurement of that particular quality or as part of an array with respect to a determining a variety of qualities utilizing various differential techniques. The present invention may be implemented in a variety of different operating environments including but not limited to gasoline engines, diesel engines, transmissions, turbines, transformers, gear boxes, vacuum pumps and other oil-reliant machinery.

Some embodiments of the present invention may employ various means of metal detection. For example, metal detection may be electrical; attaching a specific ion to a polystyrene bead may allow for a specific metal or group of metals to be detected. In one such example, one chamber of a sensor may contain beads with a hydrogen ion while the other chamber may contain beads with a barium ion. The sensor may be placed in an oil solution that contains lead whereby the lead would displace the hydrogen ion and electrically 'cap' the bead so that it does not change conductivity when polarity changes. The barium, on the other hand, would not be affected by the lead and will change conductivity only when the oil polarity changes. Taking the electrical differential of the signals generated by the beads in the two chambers will provide an indication of the lead contamination.

Metal detection may also be visible. For example, in the presence of copper, a colorimetric change takes place when the hydrogen ion is replaced by a copper ion. While the copper will replace the hydrogen ion, the barium ion will not be replaced. Measuring the differential of the visible spectra of the two chambers may provide an indication of, in this example, copper contamination in the oil.

Detection may also occur mechanically or electro-mechanically. The bead size may change by, for example, 5% when different ions are attached. Using a mechanical differential measurement methodology may provide an indication of specific metals. A spring or fulcrum may be used in some embodiments to show this differential.

In a still further embodiment of the present invention, a method for measuring fuel contamination in oil uses a material in contact with the oil. Fuel intrusion into the oil will change the electrical, mechanical and/or chemical properties of the material as compared to the same electrical, mechanical, and/or chemical properties of the material when in contact with mineral or synthetic oil only. The measured property of the material that is in contact with the oil/fuel mixture will change with respect to fuel; oil will not change the property.

In such an embodiment, the material may be a plastic comprised of a homologous polymer of polystyrene and polyphenylene oxide, which is commercially available under the brand name Noryl. In another embodiment, the material may be a high molecular weight silicone paste. Noryl shows excellent tolerance for mineral oils while showing extreme intolerance (softening) for fuel. Silicone or fluorosilicone paste is a non-polar substance that is susceptible to swelling and even dissolving in solvents and fuels while the effect of mineral and synthetic oil on silicone is minimal.

The polystyrene in Noryl can be mixed with other materials either during polymerization or post polymerization to enhance its susceptibility to fuel and change its electrical properties. For example, polystyrene co-polymerized and cross-linked with divinyl benzene (DVB) can be used. The amount of DVB used during polymerization can change how the resulting polymer reacts to oil versus fuel. The material could be in the form of an ion exchange resin bead (e.g., sulfonated or aminated Polystyrene/DVB) with a chosen substance attached to the ion exchange sites where the fuel will cause a measurable change in electrical, mechanical, or chemical properties of the ion exchange resin bead. Silicone can be doped with different substances to enhance its electrical properties (e.g., resistance and capacitance), mechanical properties (e.g., viscosity and durometry), and chemical properties (e.g., solubility and reactivity).

The material is physically small enough to be placed in some type of sense element that can be in contact with the fuel/oil mixture in situ. The material could be utilized in a probe. The material (silicone or polystyrene) could also be in the form of a thin substrate bonded to a stiff backbone with two probes on each side (or end) of the substrate. The probes could measure the impedance, capacitance, or resistance of the substrate (similar to the thin polystyrene substrate used by multiple companies to detect water in oil by measuring the change in capacitance of the polystyrene). The probes could be spring loaded where the substrate disintegrates in the fuel/oil mixture and the probes would form a hard contact.

The system could take the form of a coating that is deposited over a conductive or semi-conductive material causing a change in the electrical properties or mechanical properties of the system as the physical or electrical properties of the material change due to the change in the coating as it comes in contact with fuel.

The material could be in the form of polymeric beads—ion exchange-functionalized or not—where fuel intruding into the oil causes a measurable change in the beads. The beads could be trapped in a mesh housing allowing contact with the oil and the mesh provides a means for measuring a chemical/electrical/mechanical change in the beads.

Figure 8:
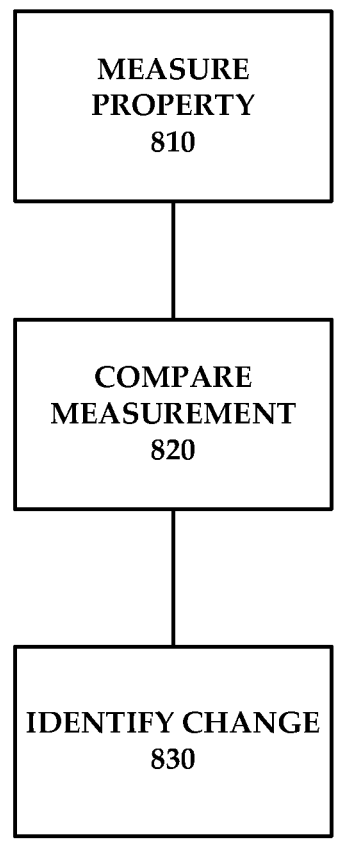
FIG. 8 discloses a method for measuring fuel contamination in oil.

FIG. 8 illustrates a method for measuring fuel contamination in oil. In step 810, an electrical, mechanical, and/or chemical property of a material in contact with oil is measured. In step 820, the measured electrical, mechanical, and/or chemical property of the material in contact with the oil is compared against a previously measured electrical, mechanical, and/or chemical property of the same material. A change is identified in the measured electrical, mechanical, and/or chemical property against the previously measured electrical, mechanical, and/or chemical property in step 830, wherein the change indicates fuel intrusion into and contamination of the oil. The existence of this intrusion may be reported to a user through an interface like that described in the context of FIG. 7.

While this invention has been described in conjunction with the specific exemplary embodiments outlined above, many alternatives, modifications, and variations may be apparent to those skilled in the art. Accordingly, the exemplary embodiments of the invention as set forth both are intended to be illustrative and not limiting except as otherwise set forth in the claims.

What is claimed is:

1. A method for measuring oil quality, the method comprising:
    measuring a property of a material in contact with oil, wherein the material is physically small enough to be placed in a sensing element having a first chamber sensitive to fuel contamination and a second chamber that is not sensitive to fuel contamination, whereby a differential signal applied to the first chamber versus that of the second chamber generates the measured property;
    comparing the measured property of the material in contact with the oil against a previously measured property of the same material, wherein the previously measured property is part of a stored series of oil analyses conducted over time;
    identifying a change in the measured property of the material as compared to the previously measured property of the material, wherein the change indicates fuel intrusion into and contamination of the oil; and
    graphically illustrating the change of the measured property by way of a light emitting diode (LED).

2. The method of claim 1, wherein the measured property of the material shows intolerance of the material to fuel.

3. The method of claim 1, wherein the material includes polystyrene.

4. The method of claim 3, wherein the material softens in the presence of fuel.

5. The method of claim 3, wherein the material is Noryl.

6. The method of claim 3, wherein the material is silicone doped with other substances.

7. The method of claim 1, wherein the material includes silicone.

8. The method of claim 7, wherein the material that includes silicone swells or dissolves in the presence of fuel.

9. The method of claim 1, wherein the material is deposited over a conductive or semi-conductive material.

10. A non-transitory computer readable storage medium having embodied thereon a program executable by a processor to perform a method for measuring oil quality, the method comprising:
    measuring a property of a material in contact with oil with one or more sensors in communication with the processor, wherein the material is physically small enough to be placed in a sensing element of the one or more sensors having a first chamber sensitive to fuel contamination and a second chamber that is not sensitive to fuel contamination, whereby a differential signal applied to the first chamber versus that of the second chamber generates the measured property;

comparing the measured property of the material in contact with the oil against a previously measured property of the same material stored in a data repository, wherein the previously measured property is part of a stored series of oil analyses conducted over time;

identifying a change in the measured property of the material as compared to the previously measured property of the material, wherein the change indicates fuel intrusion into and contamination of the oil; and generating a graphic indication of the change of the measured property by way of a light emitting diode (LED).

11. The non-transitory computer readable storage medium of claim 10, wherein the measured property of the material shows intolerance of the material to fuel.

12. The non-transitory computer readable storage medium of claim 10, wherein the material includes polystyrene.

13. The non-transitory computer readable storage medium of claim 12, wherein the material softens in the presence of fuel.

14. The non-transitory computer readable storage medium of claim 12, wherein the material is Noryl.

15. The non-transitory computer readable storage medium of claim 12, wherein the material is silicone doped with other substances.

16. The non-transitory computer readable storage medium of claim 10, wherein the material includes silicone.

17. The non-transitory computer readable storage medium of claim 16, wherein the material that includes silicone swells or dissolves in the presence of fuel.

18. The non-transitory computer readable storage medium of claim 10, wherein the material is deposited over a conductive or semi-conductive material.

* * * * *